(12) United States Patent
Toellner

(10) Patent No.: US 11,994,133 B2
(45) Date of Patent: *May 28, 2024

(54) COMPRESSIBLE AND EXPANDABLE BLADE FOR A FLUID PUMP

(71) Applicant: ECP ENTWICKLUNGSGESELLSCHAFT MBH, Aachen (DE)

(72) Inventor: Thomas Toellner, Aachen (DE)

(73) Assignee: ECP ENTWICKLUNGSGESELLSCHAFT MBH, Aachen (DE)

( * ) Notice: Subject to any disclaimer, the term of this patent is extended or adjusted under 35 U.S.C. 154(b) by 78 days.

This patent is subject to a terminal disclaimer.

(21) Appl. No.: 17/582,676

(22) Filed: Jan. 24, 2022

(65) Prior Publication Data

US 2022/0228592 A1 Jul. 21, 2022

Related U.S. Application Data

(63) Continuation of application No. 16/404,800, filed on May 7, 2019, now Pat. No. 11,268,521, which is a
(Continued)

(30) Foreign Application Priority Data

Jun. 25, 2009 (EP) .................... 09075276

(51) Int. Cl.
*A61M 60/122* (2021.01)
*A61M 60/13* (2021.01)
(Continued)

(52) U.S. Cl.
CPC ....... *F04D 15/0055* (2013.01); *A61M 60/122* (2021.01); *A61M 60/13* (2021.01); *A61M 60/174* (2021.01); *A61M 60/205* (2021.01); *A61M 60/237* (2021.01); *A61M 60/808* (2021.01); *A61M 60/857* (2021.01); *B23H 9/10* (2013.01); *B23K 26/21* (2015.10); *B23K 26/38* (2013.01); *F04D 3/00* (2013.01); *F04D 3/02* (2013.01); *F04D 29/181* (2013.01); *F04D 29/247* (2013.01); *A61M 60/135* (2021.01);
(Continued)

(58) Field of Classification Search
CPC .................... A61M 60/122; F04D 15/0055
USPC .......................................... 600/16
See application file for complete search history.

(56) References Cited

U.S. PATENT DOCUMENTS 3,510,229 A 5/1970 Smith
3,568,659 A 3/1971 Karnegis
(Continued)

FOREIGN PATENT DOCUMENTS

CA 008330 A 1/1878
CA 311977 A 6/1931
(Continued)

*Primary Examiner* — Nadia A Mahmood
(74) *Attorney, Agent, or Firm* — Botos Churchill IP Law LLP

(57) ABSTRACT

The invention relates to a compressible and expandable blade for the rotor of a fluid pump having at least two lamellae which are disposed adjacently, are pivotable respectively relative to an axis of rotation of the rotor and moveable relative to each other, and abut against each other in the expanded state of the blade such that they form together a continuous blade surface.

23 Claims, 16 Drawing Sheets

Related U.S. Application Data continuation of application No. 14/754,395, filed on Jun. 29, 2015, now Pat. No. 10,330,101, which is a continuation of application No. 13/261,100, filed as application No. PCT/EP2010/004023 on Jun. 25, 2010, now Pat. No. 9,067,006.

(60) Provisional application No. 61/220,292, filed on Jun. 25, 2009.

(51) Int. Cl.

| | | |
|---|---|---|
| *A61M 60/174* | (2021.01) | |
| *A61M 60/205* | (2021.01) | |
| *A61M 60/237* | (2021.01) | |
| *A61M 60/808* | (2021.01) | |
| *A61M 60/857* | (2021.01) | |
| *B23H 9/10* | (2006.01) | |
| *B23K 26/21* | (2014.01) | |
| *B23K 26/38* | (2014.01) | |
| *F04D 3/00* | (2006.01) | |
| *F04D 3/02* | (2006.01) | |
| *F04D 15/00* | (2006.01) | |
| *F04D 29/18* | (2006.01) | |
| *F04D 29/24* | (2006.01) | |
| *A61M 60/135* | (2021.01) | |
| *A61M 60/148* | (2021.01) | |
| *A61M 60/414* | (2021.01) | |

(52) U.S. Cl.
CPC ......... *A61M 60/148* (2021.01); *A61M 60/414* (2021.01); *A61M 2207/00* (2013.01); *Y10T 29/49337* (2015.01)

(56) References Cited

U.S. PATENT DOCUMENTS

| | | |
|---|---|---|
| 3,802,551 A | 4/1974 | Somers |
| 3,812,812 A | 5/1974 | Hurwitz |
| 4,014,317 A | 3/1977 | Bruno |
| 4,207,028 A | 6/1980 | Ridder |
| 4,559,951 A | 12/1985 | Dahl et al. |
| 4,563,181 A | 1/1986 | Wijayarathna et al. |
| 4,679,558 A | 7/1987 | Kensey et al. |
| 4,686,982 A | 8/1987 | Nash |
| 4,747,821 A | 5/1988 | Kensey et al. |
| 4,749,376 A | 6/1988 | Kensey et al. |
| 4,753,221 A | 6/1988 | Kensey et al. |
| 4,801,243 A | 1/1989 | Norton |
| 4,817,613 A | 4/1989 | Jaraczewski et al. |
| 4,919,647 A | 4/1990 | Nash |
| 4,957,504 A | 9/1990 | Chardack |
| 4,969,865 A | 11/1990 | Hwang et al. |
| 4,995,857 A | 2/1991 | Arnold |
| 5,011,469 A | 4/1991 | Buckberg et al. |
| 5,040,944 A | 8/1991 | Cook |
| 5,042,984 A | 8/1991 | Kensey et al. |
| 5,052,404 A | 10/1991 | Hodgson |
| 5,061,256 A | 10/1991 | Wampler |
| 5,092,844 A | 3/1992 | Schwartz et al. |
| 5,097,849 A | 3/1992 | Kensey et al. |
| 5,108,411 A | 4/1992 | Mckenzie |
| 5,112,292 A | 5/1992 | Hwang et al. |
| 5,113,872 A | 5/1992 | Jahrmarkt et al. |
| 5,117,838 A | 6/1992 | Palmer et al. |
| 5,118,264 A | 6/1992 | Smith |
| 5,145,333 A | 9/1992 | Smith |
| 5,151,721 A | 9/1992 | Allendorf et al. |
| 5,163,910 A | 11/1992 | Schwartz et al. |
| 5,169,378 A | 12/1992 | Figuera |
| 5,183,384 A | 2/1993 | Trumbly |
| 5,191,888 A | 3/1993 | Palmer et al. |
| 5,201,679 A | 4/1993 | Velte et al. |
| 5,275,580 A | 1/1994 | Yamazaki |
| 5,373,619 A | 12/1994 | Fleischhacker et al. |
| 5,376,114 A | 12/1994 | Jarvik |
| 5,501,574 A | 3/1996 | Raible |
| 5,531,789 A | 7/1996 | Yamazaki et al. |
| 5,701,911 A | 12/1997 | Sasamine et al. |
| 5,749,855 A | 5/1998 | Reitan |
| 5,755,784 A | 5/1998 | Jarvik |
| 5,776,190 A | 7/1998 | Jarvik |
| 5,813,405 A | 9/1998 | Montano et al. |
| 5,820,571 A | 10/1998 | Erades et al. |
| 5,851,174 A | 12/1998 | Jarvik et al. |
| 5,877,566 A | 3/1999 | Chen |
| 5,882,329 A | 3/1999 | Patterson et al. |
| 5,888,241 A | 3/1999 | Jarvik |
| 5,938,672 A | 8/1999 | Nash |
| 6,030,397 A | 2/2000 | Monetti et al. |
| 6,129,704 A | 10/2000 | Forman et al. |
| 6,152,693 A | 11/2000 | Olsen et al. |
| 6,168,624 B1 | 1/2001 | Sudai |
| 6,254,359 B1 | 7/2001 | Aber |
| 6,302,910 B1 | 10/2001 | Yamazaki et al. |
| 6,308,632 B1 | 10/2001 | Shaffer |
| 6,336,939 B1 | 1/2002 | Yamazaki et al. |
| 6,346,120 B1 | 2/2002 | Yamazaki et al. |
| 6,387,125 B1 | 5/2002 | Yamazaki et al. |
| 6,503,224 B1 | 1/2003 | Forman et al. |
| 6,506,025 B1 | 1/2003 | Gharib |
| 6,508,787 B2 | 1/2003 | Erbel et al. |
| 6,517,315 B2 | 2/2003 | Belady |
| 6,527,521 B2 | 3/2003 | Noda |
| 6,533,716 B1 | 3/2003 | Schmitz-rode et al. |
| 6,537,030 B1 | 3/2003 | Garrison |
| 6,537,315 B2 | 3/2003 | Yamazaki et al. |
| 6,592,612 B1 | 7/2003 | Samson et al. |
| 6,652,548 B2 | 11/2003 | Evans et al. |
| 6,719,791 B1 | 4/2004 | Nuesser et al. |
| 6,790,171 B1 | 9/2004 | Gruendeman et al. |
| 6,860,713 B2 | 3/2005 | Hoover |
| 6,945,977 B2 | 9/2005 | Demarais et al. |
| 6,981,942 B2 | 1/2006 | Khaw et al. |
| 7,022,100 B1 | 4/2006 | Aboul-hosn et al. |
| 7,027,875 B2 | 4/2006 | Siess et al. |
| 7,054,156 B2 | 5/2006 | Espinoza-ibarra et al. |
| 7,074,018 B2 | 7/2006 | Chang |
| 7,179,273 B1 | 2/2007 | Palmer et al. |
| 7,393,181 B2 | 7/2008 | Mcbride et al. |
| 7,467,929 B2 | 12/2008 | Nuesser et al. |
| 7,731,675 B2 | 6/2010 | Aboul-hosn et al. |
| 7,841,976 B2 | 11/2010 | Mcbride et al. |
| 7,927,068 B2 | 4/2011 | Mcbride et al. |
| 7,934,909 B2 | 5/2011 | Nuesser et al. |
| 8,079,948 B2 | 12/2011 | Shifflette |
| 2002/0094273 A1 | 7/2002 | Huang |
| 2002/0123661 A1 | 9/2002 | Verkerke et al. |
| 2003/0135086 A1 | 7/2003 | Khaw et al. |
| 2003/0231959 A1 | 12/2003 | Snider |
| 2004/0044266 A1 | 3/2004 | Siess et al. |
| 2004/0046466 A1 | 3/2004 | Siess et al. |
| 2004/0093074 A1 | 5/2004 | Hildebrand et al. |
| 2004/0215222 A1 | 10/2004 | Krivoruchko |
| 2004/0215228 A1 | 10/2004 | Simpson et al. |
| 2005/0101200 A1 | 5/2005 | Townsend |
| 2006/0008349 A1 | 1/2006 | Khaw |
| 2006/0062672 A1 | 3/2006 | Mcbride et al. |
| 2006/0195004 A1 | 8/2006 | Jarvik |
| 2007/0270875 A1 | 11/2007 | Bacher et al. |
| 2008/0073983 A1 | 3/2008 | Krajcir |
| 2008/0103591 A1 | 5/2008 | Siess |
| 2008/0132747 A1 | 6/2008 | Shifflette |
| 2008/0132748 A1 | 6/2008 | Shifflette |
| 2008/0262584 A1 | 10/2008 | Bottomley et al. |
| 2008/0306327 A1 | 12/2008 | Shifflette |
| 2009/0060743 A1 | 3/2009 | Mcbride et al. |
| 2009/0062597 A1 | 3/2009 | Shifflette |
| 2009/0093764 A1 | 4/2009 | Pfeffer et al. |
| 2009/0093796 A1 | 4/2009 | Pfeffer et al. |
| 2010/0041939 A1 | 2/2010 | Siess |
| 2010/0268017 A1 | 10/2010 | Siess |

(56) References Cited

U.S. PATENT DOCUMENTS

| | | |
|---|---|---|
| 2011/0071338 A1 | 3/2011 | Mcbride et al. |
| 2011/0236210 A1 | 9/2011 | Mcbride et al. |
| 2011/0238172 A1 | 9/2011 | Akdis |
| 2011/0257462 A1 | 10/2011 | Rodefeld et al. |
| 2011/0275884 A1 | 11/2011 | Scheckel |
| 2012/0039711 A1 | 2/2012 | Roehn |
| 2012/0039713 A1 | 2/2012 | Shifflette |
| 2012/0041254 A1 | 2/2012 | Scheckel |
| 2012/0046648 A1 | 2/2012 | Scheckel |
| 2012/0093628 A1 | 4/2012 | Liebing |
| 2012/0101455 A1 | 4/2012 | Liebing |
| 2012/0142994 A1 | 6/2012 | Toellner |
| 2012/0184803 A1 | 7/2012 | Simon et al. |
| 2012/0224970 A1 | 9/2012 | Schumacher et al. |
| 2012/0234411 A1 | 9/2012 | Scheckel |
| 2012/0237353 A1 | 9/2012 | Schumacher et al. |
| 2012/0237357 A1 | 9/2012 | Schumacher et al. |
| 2012/0264523 A1 | 10/2012 | Liebing |
| 2012/0265002 A1 | 10/2012 | Roehn et al. |
| 2012/0294727 A1 | 11/2012 | Roehn |
| 2012/0301318 A1 | 11/2012 | Er |
| 2012/0308406 A1 | 12/2012 | Schumacher |
| 2013/0019968 A1 | 1/2013 | Liebing |
| 2013/0041202 A1 | 2/2013 | Toellner |
| 2013/0060077 A1 | 3/2013 | Liebing |
| 2013/0066139 A1 | 3/2013 | Wiessler et al. |
| 2013/0085318 A1 | 4/2013 | Toellner |
| 2013/0177409 A1 | 7/2013 | Schumacher et al. |
| 2013/0177432 A1 | 7/2013 | Toellner et al. |
| 2013/0204362 A1 | 8/2013 | Toellner et al. |
| 2013/0237744 A1 | 9/2013 | Pfeffer et al. |
| 2014/0039465 A1 | 2/2014 | Schulz et al. |

FOREIGN PATENT DOCUMENTS

| | | |
|---|---|---|
| CA | 701809 A | 1/1965 |
| CA | 701810 A | 1/1965 |
| DE | 2207296 A1 | 8/1972 |
| DE | 2113986 A1 | 9/1972 |
| DE | 2233293 A1 | 1/1973 |
| DE | 2613696 A1 | 10/1977 |
| DE | 4124299 A1 | 1/1992 |
| DE | 69103295 T2 | 12/1994 |
| DE | 69017784 T2 | 11/1995 |
| DE | 19535781 A1 | 3/1997 |
| DE | 19711935 A1 | 4/1998 |
| DE | 29804046 U1 | 4/1998 |
| DE | 69407869 T2 | 4/1998 |
| DE | 69427390 T2 | 9/2001 |
| DE | 10059714 C1 | 5/2002 |
| DE | 10108810 A1 | 8/2002 |
| DE | 10155011 A1 | 5/2003 |
| DE | 69431204 T2 | 8/2003 |
| DE | 10336902 B3 | 8/2004 |
| DE | 102010011998 A1 | 9/2010 |
| EP | 0364293 A2 | 4/1990 |
| EP | 0480102 A1 | 4/1992 |
| EP | 0560000 A2 | 9/1993 |
| EP | 0629412 A2 | 12/1994 |
| EP | 0768091 A1 | 4/1997 |
| EP | 0884064 A2 | 12/1998 |
| EP | 0914171 A2 | 5/1999 |
| EP | 0916359 A1 | 5/1999 |
| EP | 951302 A2 | 10/1999 |
| EP | 1019117 A1 | 7/2000 |
| EP | 1061968 A1 | 12/2000 |
| EP | 1066851 A1 | 1/2001 |
| EP | 1114648 A2 | 7/2001 |
| EP | 1337288 A1 | 8/2003 |
| EP | 1651290 A1 | 5/2006 |
| EP | 2218469 A1 | 8/2010 |
| EP | 2047872 B1 | 9/2010 |
| EP | 2229965 A1 | 9/2010 |
| EP | 2301598 A1 | 3/2011 |
| EP | 2308524 A1 | 4/2011 |
| EP | 2343091 A1 | 7/2011 |
| EP | 2345440 A1 | 7/2011 |
| EP | 2366412 A2 | 9/2011 |
| EP | 2497521 A1 | 9/2012 |
| EP | 2606919 A1 | 6/2013 |
| EP | 2606920 A1 | 6/2013 |
| EP | 2607712 A1 | 6/2013 |
| GB | 2239675 A | 7/1991 |
| GB | 2405677 A | 3/2005 |
| RU | 2229899 C2 | 6/2004 |
| WO | 9202263 A1 | 2/1992 |
| WO | 9302732 A1 | 2/1993 |
| WO | 9303786 A1 | 3/1993 |
| WO | 9314805 A1 | 8/1993 |
| WO | 94001148 A1 | 1/1994 |
| WO | 9405347 A1 | 3/1994 |
| WO | 9409835 A1 | 5/1994 |
| WO | 9420165 A2 | 9/1994 |
| WO | 9523000 A2 | 8/1995 |
| WO | 9618358 A1 | 6/1996 |
| WO | 9625969 A2 | 8/1996 |
| WO | 9744071 A1 | 11/1997 |
| WO | 9853864 A1 | 12/1998 |
| WO | 9919017 A1 | 4/1999 |
| WO | 0027446 A1 | 5/2000 |
| WO | 0043054 A2 | 7/2000 |
| WO | 0062842 A1 | 10/2000 |
| WO | 2001007760 A1 | 2/2001 |
| WO | 2001007787 A1 | 2/2001 |
| WO | 2001083016 A2 | 11/2001 |
| WO | 03057013 A2 | 7/2003 |
| WO | 2003103745 A2 | 12/2003 |
| WO | 2005002646 A1 | 1/2005 |
| WO | 2005016416 A1 | 2/2005 |
| WO | 2005021078 A1 | 3/2005 |
| WO | 2005030316 A1 | 4/2005 |
| WO | 2005032620 A1 | 4/2005 |
| WO | 2005081681 A2 | 9/2005 |
| WO | 2006020942 A1 | 2/2006 |
| WO | 2006034158 A2 | 3/2006 |
| WO | 2006051023 A1 | 5/2006 |
| WO | 2006133209 A1 | 12/2006 |
| WO | 2007003351 A1 | 1/2007 |
| WO | 2007103390 A2 | 9/2007 |
| WO | 2007103464 A2 | 9/2007 |
| WO | 2007112033 A2 | 10/2007 |
| WO | 2008017289 A1 | 2/2008 |
| WO | 2008034068 A2 | 3/2008 |
| WO | 2008054699 A2 | 5/2008 |
| WO | 2008106103 A2 | 9/2008 |
| WO | 2008116765 A2 | 10/2008 |
| WO | 2008124696 A1 | 10/2008 |
| WO | 2008137352 A1 | 11/2008 |
| WO | 2008137353 A1 | 11/2008 |
| WO | 2009015784 A1 | 2/2009 |
| WO | 2009029959 A2 | 3/2009 |
| WO | 2009073037 A1 | 6/2009 |
| WO | 2010133567 A1 | 11/2010 |
| WO | 2013034547 A1 | 3/2013 |
| WO | 2013092971 A1 | 6/2013 |
| WO | 2013093001 A2 | 6/2013 |
| WO | 2013093058 A1 | 6/2013 |

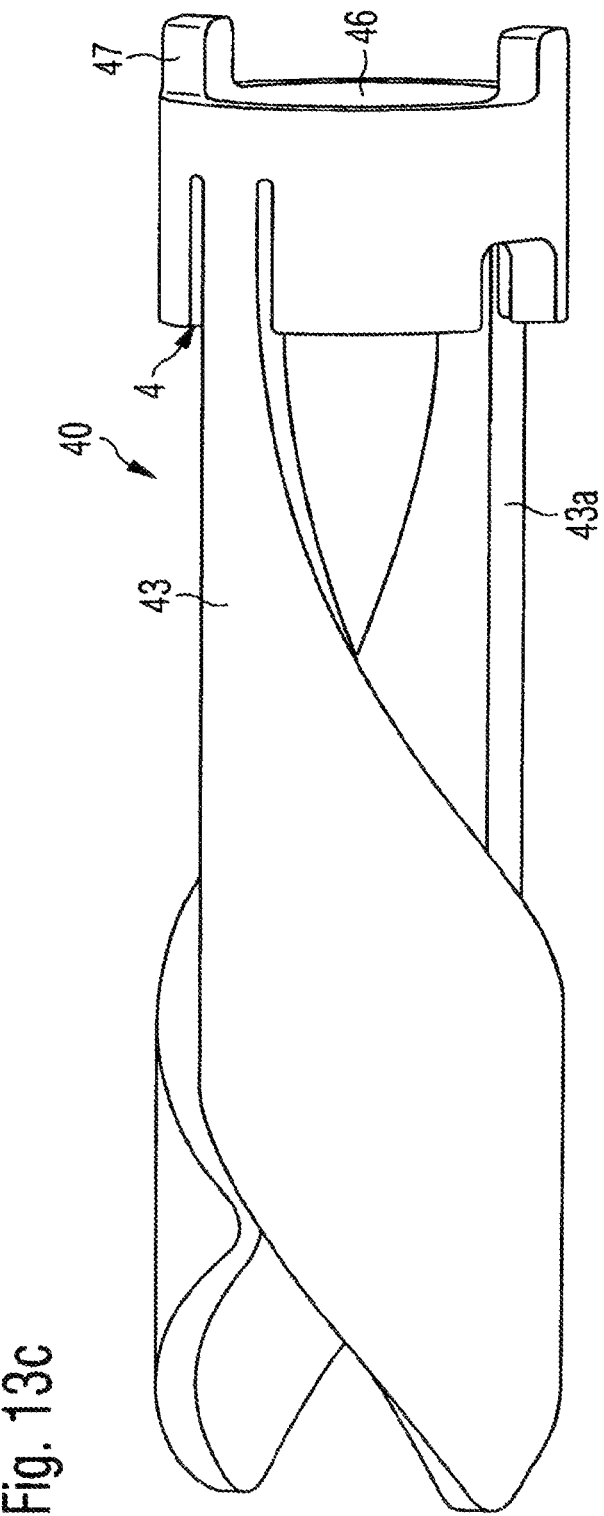

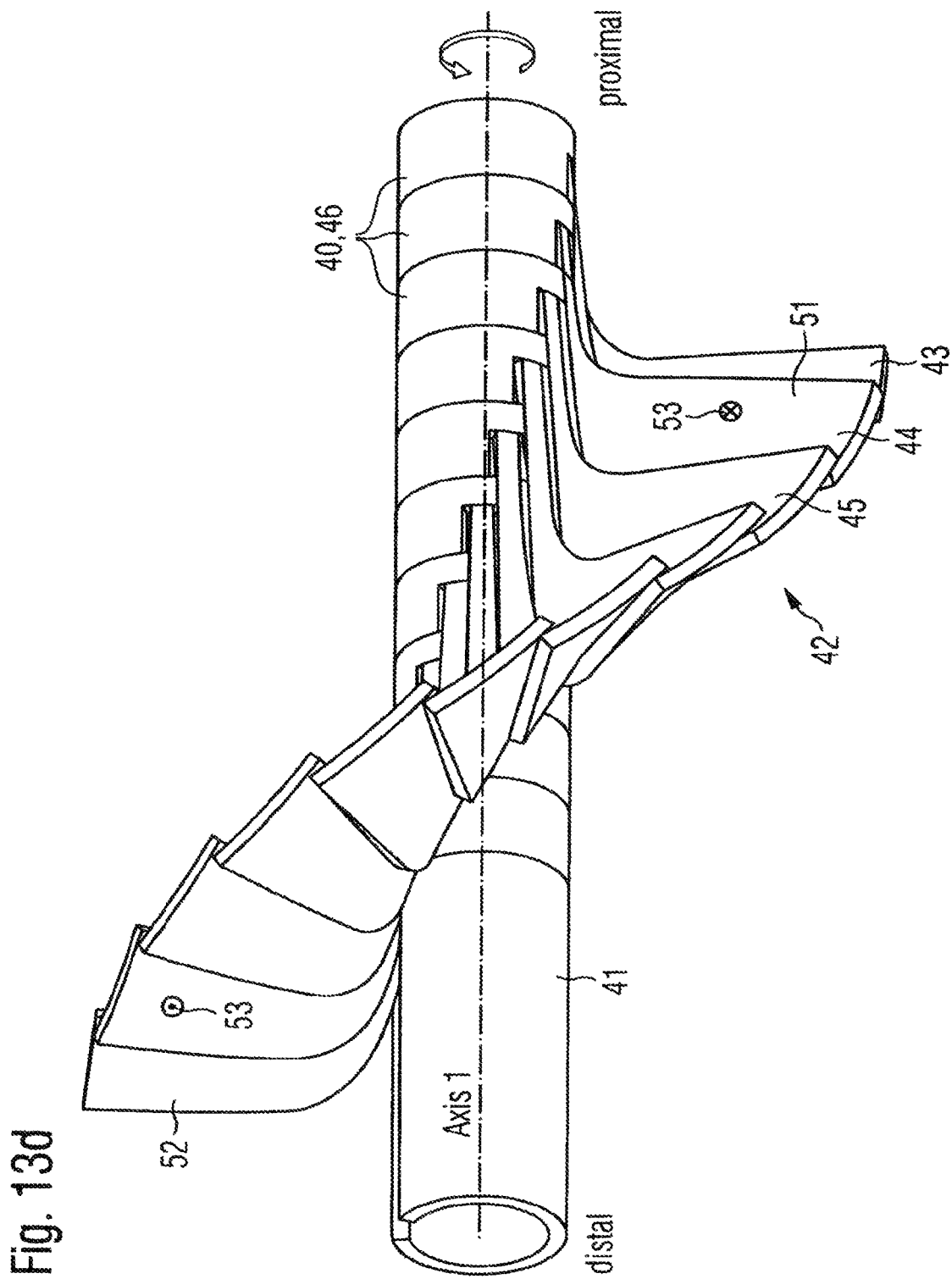

COMPRESSIBLE AND EXPANDABLE BLADE FOR A FLUID PUMP

CROSS-REFERENCE TO RELATED APPLICATIONS

The present application is a continuation of U.S. patent application Ser. No. 16/404,800, filed May 7, 2019, now U.S. Pat. No. 11,268,521, which is a continuation of U.S. patent application Ser. No. 14/754,395, filed Jun. 29, 2015, now U.S. Pat. No. 10,330,101, which is a continuation of U.S. patent application Ser. No. 13/261,100, filed Feb. 16, 2012, now U.S. Pat. No. 9,067,006, which is a national phase entry under 35 U.S.C. § 371 of International Application No. PCT/EP2010/004023, filed Jun. 25, 2010, published as International Publication No. WO 2010/149393 A1, which claims the benefit of the filing date of U.S. Provisional Patent Application No. 61/220,292, filed Jun. 25, 2009, and priority to European Patent Application No. 09075276.7, filed Jun. 25, 2009, the disclosures of which are hereby incorporated herein by reference.

BACKGROUND OF THE INVENTION

The present invention resides in the field of mechanics or micromechanics and can be applied advantageously in particular in medical technology.

The invention relates to a blade for a pump and the design thereof. Of concern thereby is a pump having a rotor, the rotor being compressible and expandable in order to be able possibly to change the overall dimensions of the pump. In this way, the pump can be pushed through not readily accessible openings or into narrow pipe systems, for which purpose it is firstly compressed and, after it has been moved to the location of use, is expanded again.

Such a pump can be used particularly advantageously in medical technology in the field of heart pumps or other pumps for body fluids which are normally used with catheters.

In the technical medical field, different types of micropumps are known, which pumps can be introduced in the compressed state with a catheter through a naturally occurring body vessel into the body of a patient and can be expanded in situ. In order to produce a corresponding radial compressibility and expandability, various effects can be used in the construction and the structure of the pump housing and the pump rotor, such as e.g., the use of so-called memory alloys which change their shape as a function of the ambient temperature or control the pump diameter specifically by providing specific transmission mechanisms which allow it.

A solution is known from DE 10 2004 054 714 A1 in which both the impeller of a micropump and the housing thereof is manipulated by a mutual axial displacement of the pump drive shaft. As a result, the housing is changed between a compressed and an expanded state.

A system is known from the patent document WO 00/2003103745 A2, in which the pump housing is like-wise expanded mutually radially by an axial relative movement of two components.

A rotor is known from the US patent specification U.S. Pat. No. 7,393,181, the blade of which can be subdivided into a plurality of partial blades or rows of partial blades for improved compressibility/collapsibility. As a result of the subdivision, the individual partial blades are smaller than a one-part blade and almost flat so that they can be rolled in easily. However, the ability to be subdivided is restricted by the intrinsic stability of the partial blades which requires to be ensured.

BRIEF SUMMARY OF THE INVENTION

With the background of the state of the art, the object underlying the present invention is to produce a rotor which can be produced as simply and economically as possible or a blade for such a rotor, high compressibility being paramount with as little as possible of a force expenditure so that, in order to withdraw the pump from the vessel, the compression of the pump rotor can be achieved without greater external resistances. In addition, the corresponding pump is intended to be designed to be efficient and low-consumption.

The object is achieved according to the invention by the features of patent claim 1.

The invention provides a blade having a plurality of lamellae which are disposed adjacently, are moveable relative to each other and pivotable relative to an axis of rotation of the rotor, the lamellae abutting against each other in the expanded state of the blade such that they form together a continuous blade surface.

Due to their pivotability, lamellae of this type can be pivoted individually very easily into a space-saving state and, in the pivoted-out, expanded state of the blade or of the rotor, form a closed blade surface which is designed such that it fulfils the required technical flow conditions with respect to shape and surface design.

Relative to a collapsible membrane, the blade consisting of individual lamellae has the advantage that its components can, both in the compressed and in the expanded state, assume a defined shape and arrangement. The individual lamellae can respectively be mounted rotatably on the shaft of the rotor and in fact advantageously pivotable in a plane which includes the longitudinal axis of the rotor shaft or an axis parallel to such a shaft, the mounting points being able to extend around the rotor shaft in a spiral in order to produce a spiral blade in the unfolded state. However, also other types of mounting are conceivable, in which the lamellae are mounted for example on one or more webs or transverse spars which are connected, for their part, to the rotor shaft.

The individual lamellae can be of equal length but can also be designed to be of different lengths according to which final shape the blade is intended to assume. The pivotability of the individual lamellae is restricted so that these, in the opened state, can withstand the flow counterpressure of a fluid to be conveyed. However, the lamellae can also be mutually supported in that they abut against each other and possibly engage in each other forming a lock. For example, the lamellae can be designed in the manner of the elements of a bird feather, the quill of the feather corresponding comparatively to the rotor shaft.

The construction of the blade can be designed such that the blade expands during rotation in the operating direction due to the fluid counterpressure and, when rotating in the opposite direction, is compressed by the effect of the medium in which the blade moves. This makes the compression and expansion movement particularly simple without greater forces requiring to be overcome. During application in the medical field, such a pump can hence be removed again in a simple manner and without the danger of damaging body vessels.

A particular embodiment of the invention provides that at least two lamellae, in particular each of the lamellae, have per se a dimensionally stable, in particular rigid configuration.

The blade obtains its flexibility not from the flexibility of a membrane but from the movability of the individual lamellae relative to each other. For this purpose, the lamellae must not exceed a specific width. Advantageously, the blade for example can consist of at least 10 or at least 50 lamellae. Such a blade can have in total a very small constructional size in order to be inserted into a blood vessel, preferably less than 5 mm for example in the compressed state, a diameter of 2 mm.

A further advantageous embodiment of the invention can provide that respectively adjacent lamellae abut against each other to form a seal along a longitudinal side which extends at least partially radially relative to the rotor axis.

If it is even conceivable that the lamellae leave intermediate spaces between themselves, then the efficiency of the fluid pump in fact increases with the seal of the blade formed by the lamellae. It is therefore advantageous if the lamellae abut against each other respectively on their longitudinal side and as far as possible leave no intermediate space there.

It can be provided in addition that respectively lamellae which are mutually directly adjacent abut against each other in such a manner that they are not pivotable relative to each other about the rotor axis in at least one direction. Hence, the individual lamellae can support each other mutually and, during operation, entirely withstand the counterpressure of the fluid to be pumped. In particular if the lamellae are distributed in a spiral on the circumference of the rotor shaft, support is provided in the azimuthal direction.

The invention can be designed in addition such that respectively adjacent lamellae mutually overlap in the region of the longitudinal side. As a result of overlapping of the lamellae, particularly high impermeability is produced and, in addition, the support function of the lamellae can be mutually exerted in the overlapping region.

Particularly high stability and impermeability between the lamellae is achieved in that respectively adjacent lamellae engage one in the other in the region of the longitudinal side. Any type of form-fitting design of adjacent lamellae can thereby be provided, for example respectively the provision of a fold along the longitudinal sides of the lamellae, for example also in the form of a thin sealing lip.

In order to produce a form-fitting and sealed connection, it can also be provided that at least one lamella, in particular all the lamellae, have a convex shape, in cross-section, on one of the longitudinal sides thereof and a concave shape on the other longitudinal side. The corresponding convex or concave structure can, in cross-section, be round, elliptical or also configured as a groove or notch.

Advantageously, respectively adjacent lamellae can be connected to each other by a flexible element, in particular a strip or a membrane. The ability of the blade to be opened out is then produced in the manner of a fan, in the case of which broad, rigid support bars are connected to each other by narrow membranes or strips.

In order to stabilize the individual lamellae these can respectively have a stiffening structure in cross-section, which provides for example a web extending in the longitudinal direction. However, it can also be provided that, additionally or alternatively, the individual lamellae are configured to be hollow with a round or square cross-section.

Advantageously, the invention can be configured by a blade in which at least two lamellae are connected to each other by a chain-like connection. Such a chain-like connection consists of small hook-like elements on the one side and blade-like elements on the respectively other side, which can be configured advantageously to be microscopically small.

The invention can furthermore be designed advantageously in that the connection is detachable by applying a load on the blade in the axial direction of the rotor and/or by a relative movement of two adjacent lamellae along their respective longitudinal sides and in the longitudinal direction of the lamellae.

The longitudinal direction of the lamellae is thereby dictated by the direction in which the respective lamella extends away from the rotor shaft.

As a result of the described structure of a blade for the rotor of a fluid pump, said blade can be designed to be particularly stable and compressible in a defined manner, as a result of which in particular good compressibility and a small final diameter of the rotor can be achieved in the compressed form.

A development provides that a compressible and expandable blade for the rotor of a fluid pump, in particular a catheter pump, is provided, at least two lamellae which are disposed adjacently being pivotable respectively relative to an axis of rotation of the rotor and being moveable relative to each other and abutting against each other in the expanded state in such a manner that they form together a continuous blade surface, the at least two adjacently-disposed lamellae belonging to different rotor segments, one rotor segment comprising at least one lamella and also a hub segment.

As a result, it becomes possible to construct a rotor "sequentially", layering of individual rotor segments hereby being provided in the axial direction. These rotor segments need not be (but might) welded etc. to each other, it suffices that these are fixed non-rotatably relative to each other. As a result of the fact that the rotor segments have respectively at least one lamella and also one hub segment, the connection to the rotor shaft can be provided by the hub segment or the hub segment can also represent an axial portion of the rotor shaft itself. By means of the combination of different hub segments, an influence can be made on the pitch of the helix. Hence, the economical construction of a helix with an irregular pitch becomes possible, the pitch increasing advantageously in the conveying direction.

The rotor segments can be made of different materials, for example from shape memory materials, in particular shape memory metals or shape memory plastic materials. In addition to "Nitinol", polymers with the desired properties are hereby possible.

A development hereby provides that the lamellae per se are respectively individually coated and/or covered by a membrane, a connection of the coating/membrane of two adjacent lamellae being at best frictional and/or form-locking. As a result, the advantage of the "bird feather" principle is ensured, on the one hand, that the placing-around of individual lamellae frictionally (in particular when introducing into a lock) is associated with low complexity, however, on the other hand (due to the mutual support effect), a high fluid counterpressure can be produced. As a result of the fact that the individual lamellae per se (or specific groups of lamellae combined) are respectively coated individually or are covered with a membrane, it is achieved that, in the boundary region of a plurality of lamellae/lamella groups, an even better sealing effect is produced, on the one hand, by the coating/membrane and, in addition, better flow-wise or biocompatible adaptation of the blade to the medium to be conveyed (e.g., blood) becomes possible. In addition, this can mean weight and stability advantages since the lamellae per se require for example a metal frame which is then coated or sprayed over with a plastic material membrane or a polymer matrix. This is a significant improvement relative to lamella arrangements in which the entire blade, as a whole, is reshaped with a single membrane or a single spraying-around since such arrangements, during compression, require higher forces because of the limited deformability of the grouped lamellae.

A particularly advantageous development provides that the at least one lamella and also the hub segment of the rotor segment are in one part. This means that these can be produced integrally or from a unified body, preferably a pipe or a flat material (raw material). The thickness of the raw material is preferably 5 µm to 500 µm, more preferably 20 µm to 200 µm.

A development provides that at least two adjacent rotor segments are connected to each other non-rotatably in a form-fit. This can be ensured by corresponding engagement elements (raised portions/depressions). As a result, the mounting is significantly simplified in addition. One development provides that an individual rotor segment has here a single hub element and also one, two (or even more) lamellae. For example, the rotor segment can have an individual lamella, however also a "wing arrangement" is conceivable in which two lamellae (preferably situated one opposite the other) protrude. Various arrangements are possible here, above all according to how much lamella surface area is required. If in particular a lot of lamella surface area is required, a flat material or even a pipe material for example with a large diameter can be chosen, a diameter change then being able to take place later in the region of the hub segment for adaptation to the rotor shaft.

A method for the production of a rotor segment or a blade having a plurality of rotor segments provides that structures for hub segments and also lamellae are cut out (for instance by means of a laser by wire eroding or etching) from a (for instance tubular or flat) basic body, a connection web between hub segment and lamellae remaining in order to ensure the advantages of the one-part state. Subsequently, the lamellae can be plastically deformed in their radially protruding normal state by corresponding shaping tools, as a result of which they correspond to the expanded (but not yet subjected to fluid pressure) state of the subsequent blade. Subsequently, possibly a chemical etching treatment or a further laser treatment of the lamellae can be effected in order to ensure for example smooth or different surfaces in order to influence the technical flow properties of the lamella. For example, also the profile of the lamella can be adapted here to assist the flow.

Hereafter, the rotor segments can subsequently be joined axially to form a rotor shaft. Preferably, these rotor segments, even when a form-fit is provided in advance by complementary concavities/raised portions, are connected to each other by means of material joining methods, for example gluing or welding.

Another development provides that rotor segments with connection webs disposed between the rotor segments can be worked out of a flat material and are to be disposed on a rotor shaft by folding the flat material out of the surface plane in such a manner that automatically a helix shape of the blade is produced.

A further development provides that a plurality of lamellae are part of one lamella body, these being connected to each other merely in their foot region. As a result, again easy collapsibility of the lamellae is achieved since they are not connected in their end region protruding radially from the rotor (in the expanded state) and hence the lamellae can individually be deformed easily.

The lamella body can thus be introducible into a hub body such that, in the unloaded state of the outer tips of the lamellae, a helix shape of the blade is formed. For example, the hub body is configured as a shell with spiral longitudinal slots into which the lamella body is introduced so that later the hub body represents the outer circumference of the rotor shaft in the case of a finished catheter pump/fluid pump.

A further development provides that the lamella body in the foot region of the lamellae has weak portions in order to achieve higher tangential deflections of the lamellae with the same force application (compared with the state in which there are no weak portions). As a result, good rigidity of the lamella is achieved, on the one hand, relative to the fluid but, on the other hand, sufficient flexibility is ensured during the first deformation of the lamella body into the helix shape.

All of the above-mentioned lamella arrangements make it possible to produce catheter pumps for introduction into human vessels, in particular for intraventricular use, a rotor with a blade and the pump having a conveying direction for conveying body fluid and the blade hereby having a flow pressure side and a flow suction side.

A development provides that, on the flow pressure side, the proximal region of a distal lamella covers the distal region of an adjacently-situated proximal lamella. As a result, the type of "stepping" of the lamellae is fixed. The advantage is that a stepping of this kind is very blood-compatible. The erythrocytes do not collide with the step-in pumping/flow direction; instead, they "fall down the steps".

In one embodiment it is possible to finish, to coat and/or to extrusion coat/insert mold the single lamellae in a way that (at least in regions) a steady/continuous curvature of the blade on the flow pressure side and/or the flow suction side is given.

A further development provides that application of the lamellae in a compressed state is effected essentially by deflecting the lamellae. This is achieved (for example in an embodiment according to FIG. 13d) in a way that proximally of the rotor a sheath is positioned and the rotor is introduced into the sheath in proximal direction, wherein the lamellae basically one after another (first the most proximal, then the one distally neighboring the most proximal and so on) are bent (i.e., the blades are not bent in total at once, instead the lamellae are bent one after another which has the advantage of lower force requirements). The sheath may have a tube-shape cross-section.

It is also possible to provide a compressible rotor housing etc. between sheath and rotor, without changing the above principle of bending the lamellae one after another. Remark: in the context of the patent application, "bending the lamellae basically one after another" means that especially beginning (the first phase) of bending of the lamellae happens one after another. In the case of multi-blade rotors, eventually several lamellae having the same axial position are contemporaneously bent.

It may be noted once again that the above-described coating of individual lamellae or groups of lamellae can be effected with a membrane (plastic material or metal foil) or any other coating.

BRIEF DESCRIPTION OF THE DRAWINGS

The invention is shown and subsequently described in the following in a drawing with reference to an embodiment.

There are thereby shown:

FIGS. 13*a* to 13*l* an embodiment of the blades according to the invention, these blades consisting of lamellae of adjacently-situated rotor segments, FIGS. 14*a* to 14*d* embodiments of a blade in which a lamella body is inserted into a spiral incision of a shell body, and also FIGS. 15*a* and 15*b* a further embodiment of a blade which is constructed from rotor segments.

DETAILED DESCRIPTION OF THE INVENTION

Figure 1:
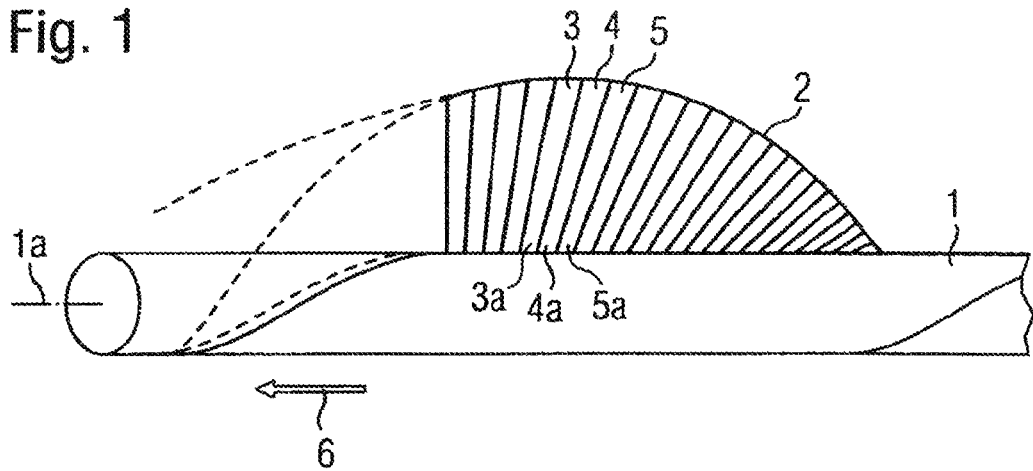
FIG. 1 schematically in a three-dimensional view, a rotor shaft and also a blade, FIG. 2 schematically, a part of a blade with a plurality of lamellae, FIG. 3 a rotor shaft in cross-section with a lamella in two positions, FIG. 4 a rotor shaft in cross-section with two lamellae in respectively two positions, FIG. 5 a view of a rotor shaft with four lamellae, FIG. 6 a view of a rotor shaft with two configurations of lamellae, FIG. 7 a view of a rotor shaft with two configurations of lamellae and also FIG. 8 a schematic representation of a heart catheter pump with a rotor and blades in a ventricle.

FIG. 1 shows a rotor shaft 1 having a blade 2 which is composed of individual, schematically indicated lamellae 3, 4, 5. The individual lamellae are mounted pivotably respectively by their feet 3*a*, 4*a*, 5*a* on the rotor shaft 1, the feet of the lamellae together extending around the rotor shaft 1 in a spiral.

In this way, a helical structure of a blade is produced, which effects an axial conveyance of a liquid in the direction of the arrow 6 during rotation about the rotor shaft 1.

Figure 2:
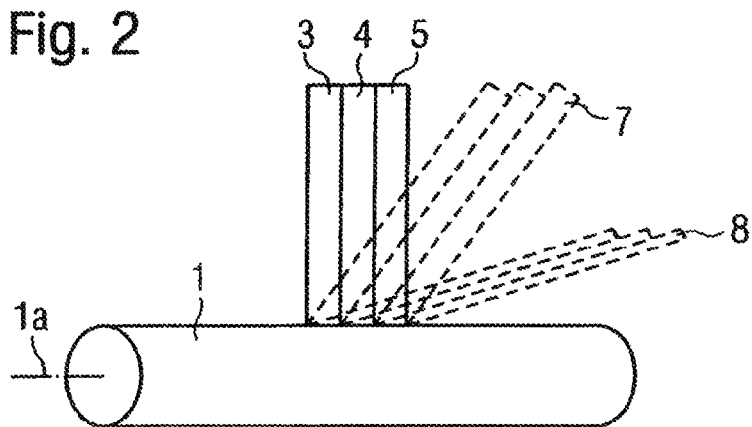

The particular embodiment of the blade according to the invention emerges in more detail from FIG. 2. In a first position, the lamellae 3, 4, 5 are represented there in the deployed, expanded shape of the blade, the adjacent lamellae abutting closely against each other by their longitudinal sides and hence forming a surface which is smooth and sealed for the flowing fluid.

In the position which is illustrated in broken lines and designated with 7, the individual lamellae are folded a little far onto the rotor shaft 1, it being totally important for the deformability of the blade that the individual lamellae 3, 4, 5 are moveable relative to each other, in particular are displaceable in the longitudinal direction. Consequently, folding of the corresponding surface is unnecessary but the individual lamellae can be folded quite far towards the rotor shaft, as is represented in the further position 8 of the lamellae.

As a result, the blade can be extensively compressed, i.e., can be reduced with respect to the radius, relative to the rotor shaft 1 or the longitudinal axis 1*a* thereof.

No noteworthy elastic counterforces are thereby produced either so that the rotor can be compressed practically without force if this is required for example for introduction or removal of a corresponding fluid pump from a naturally occurring body vessel.

Figure 3:
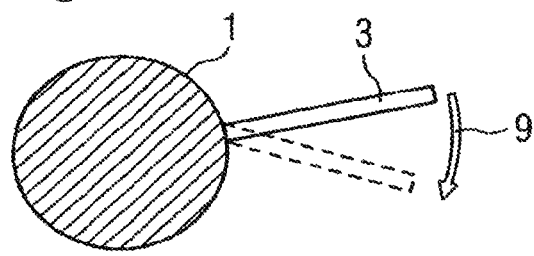

In FIG. 2, if pivotability of the individual lamellae in the longitudinal direction of the rotor shaft 1 in the plane of the rotor shaft axis is indicated, then the invention is not however restricted hereto. FIG. 3 shows pivotability of a lamella 3 in the azimuthal direction, as indicated by the arrow 9.

Figure 4:
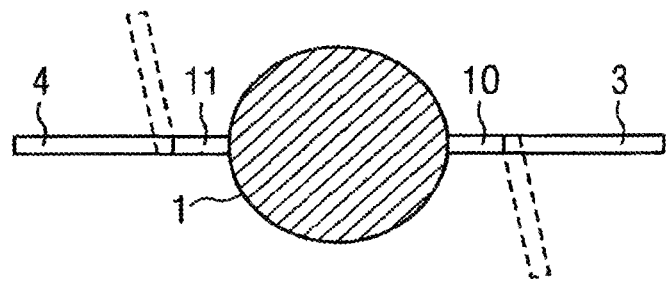

FIG. 4 shows a further variant of such an embodiment, webs 10, 11 being provided on the rotor shaft and the lamellae 3, 4 being mounted pivotably on the webs 10, 11 which extend around the rotor shaft 1 in a spiral. The pivoted positions are represented respectively in broken lines in FIG. 4.

It becomes clear that the pivoting of the lamellae in the position illustrated respectively in broken lines leads to compression of the rotor. For example, compression of the rotor can be caused by a rotational operation of the rotor in a direction opposite to the operating direction. The deployment of the rotor takes place correspondingly by rotation in the operating direction.

Basically, the individual lamellae can also be mounted on transverse spars of the rotor shaft 1 and extend in the deployed state parallel to the longitudinal axis of the rotor shaft. It is important that they can be collapsed correspondingly individually in order to reduce the diameter of the rotor.

Figure 5:
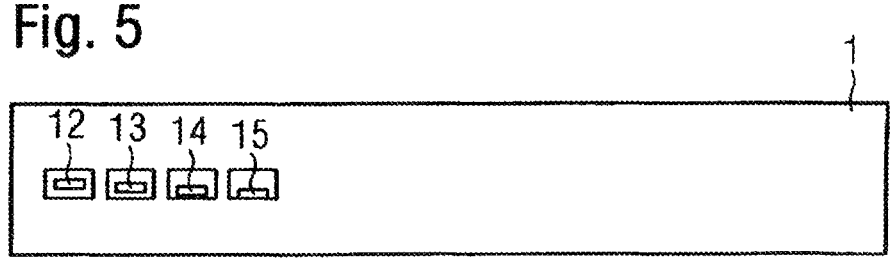

In FIG. 5, a plan view on four lamellae 12, 13, 14, 15 is shown schematically, said lamellae having respectively, in cross-section, a rectangular and hollow configuration in order to produce greater longitudinal rigidity of the individual lamellae. The objective thereby is that, despite the rigidity of the individual lamellae, the blade in total can be collapsed easily.

Figure 6:
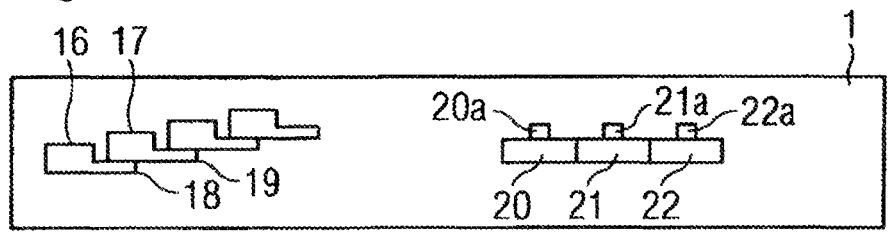

FIG. 6 shows two configurations of lamellae, on the left side respectively lamellae 16, 17 which have an overlapping lip 18, 19 being illustrated, adjacent lamellae respectively forming a seal on the overlapping lip 18, 19 of the adjacent lamella, on the one hand, and being supported, on the other hand. As a result, rigidity of the blade in total is produced so that the blade withstands an increased fluid counter-pressure during operation.

On the right side of FIG. 6, three lamellae 20, 21, 22 are illustrated, each of the lamellae having a web 20*a*, 21*a*, 22*a* extending in the radial direction of the rotor shaft 1.

Figure 7:
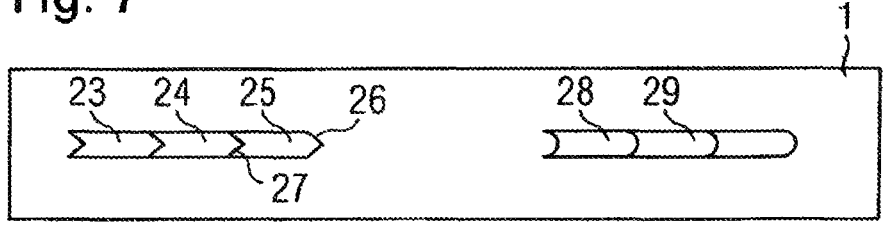

FIG. 7 shows, on left side of the plan view on the rotor shaft 1, three lamellae 23, 24, 25 which have, on one side 26, a convex protuberance and, on the other side 27, a concave depression in order that adjacent lamellae engage one in the other and thus can be mutually supported relative to an azimuthal pivoting position.

Lamellae 28, 29 are illustrated on the right side of FIG. 7, each of the lamellae having, on their longitudinal sides, a concave and a convex protuberance with a round cross-section. This design has the advantage that adjacent lamellae are rotatable about their longitudinal axis in a mutually restricted manner.

Basically, the individual lamellae can be mounted on the rotor shaft 1 either by means of a pivoting articulation or have a bendable or flexible configuration in their foot region such that they are pivotable in any case as a whole relative to the rotor shaft. The individual lamellae can also be glued by their foot ends respectively individually on a flexible strip or can be mounted on the latter in a different way, the strip with the lamellae being able as a whole to be mounted on the rotor. As a result of the flexibility of the strip, the pivotability of the individual lamellae can then be ensured.

Figure 8:
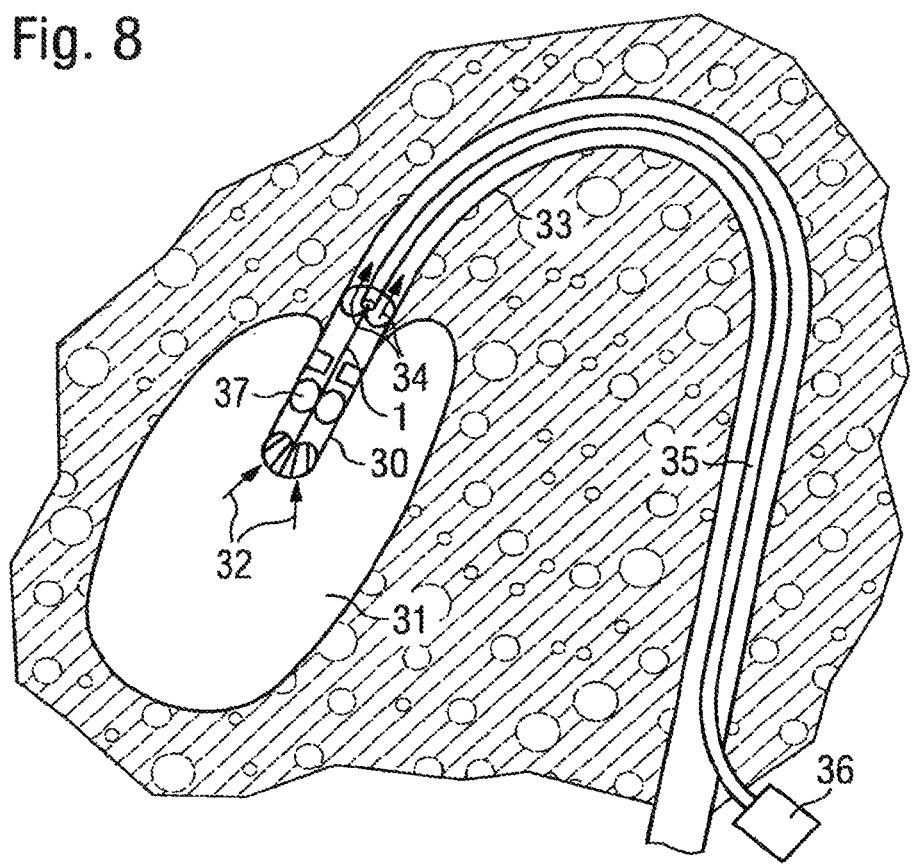

In FIG. 8, the use of a fluid pump with a blade according to the invention is represented schematically, the pump 30 being positioned in a ventricle 31 and, as indicated by the arrows 32, sucks in blood which is conveyed into a vessel 33, as is shown by the arrows 34. The pump 30 is mounted on a catheter 35, through which a shaft 1 illustrated only in the region of the pump 30 extends centrally and is actuated rotationally by means of a motor 36. The shaft moves a rotor 37 which has a blade, illustrated merely schematically.

The pump 30 in the expanded state has a diameter which can be possibly also be greater, in the extreme case, than the inner diameter of the vessel 33. For this purpose, the impeller is expanded fully. However, it can also be compressed in order to introduce or remove the pump 30, the individual lamellae, as illustrated above, being able to be folded against the rotor shaft 1 and, at the same time, the housing of the pump 30 being correspondingly collapsed. For this purpose, this housing can for example consist of a membrane which is deployed by a frame or by the fluid pressure produced in the pump 30.

Figure 9:
FIGS. 9 to 12 show schematic 3-dimensional illustrations of overlapping lamellae.

FIG. 9 shows three flat lamellae which overlap at their longitudinal sides and can have for example a burr-like connection in their overlapping region.

Figure 10:
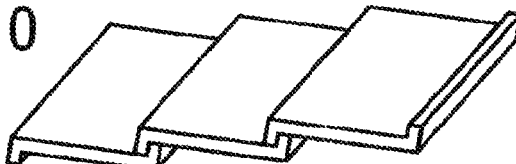
Figure 11:
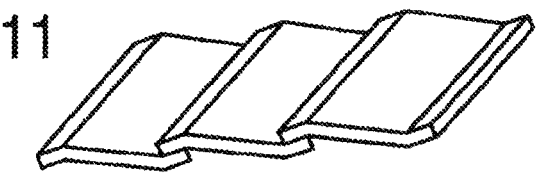

FIG. 10 shows lamellae which have edges angled by 90 degrees along their longitudinal sides respectively and with which they hook one into the other, whilst a variant, in FIG. 11, is illustrated with an angle of less than 90 degrees which likewise allows fixing of the lamellae relative to each other.

Figure 12:

FIG. 12 finally represents a variant with a curved edge which serves for the same purpose of mutual fixing.

Figure 13A:
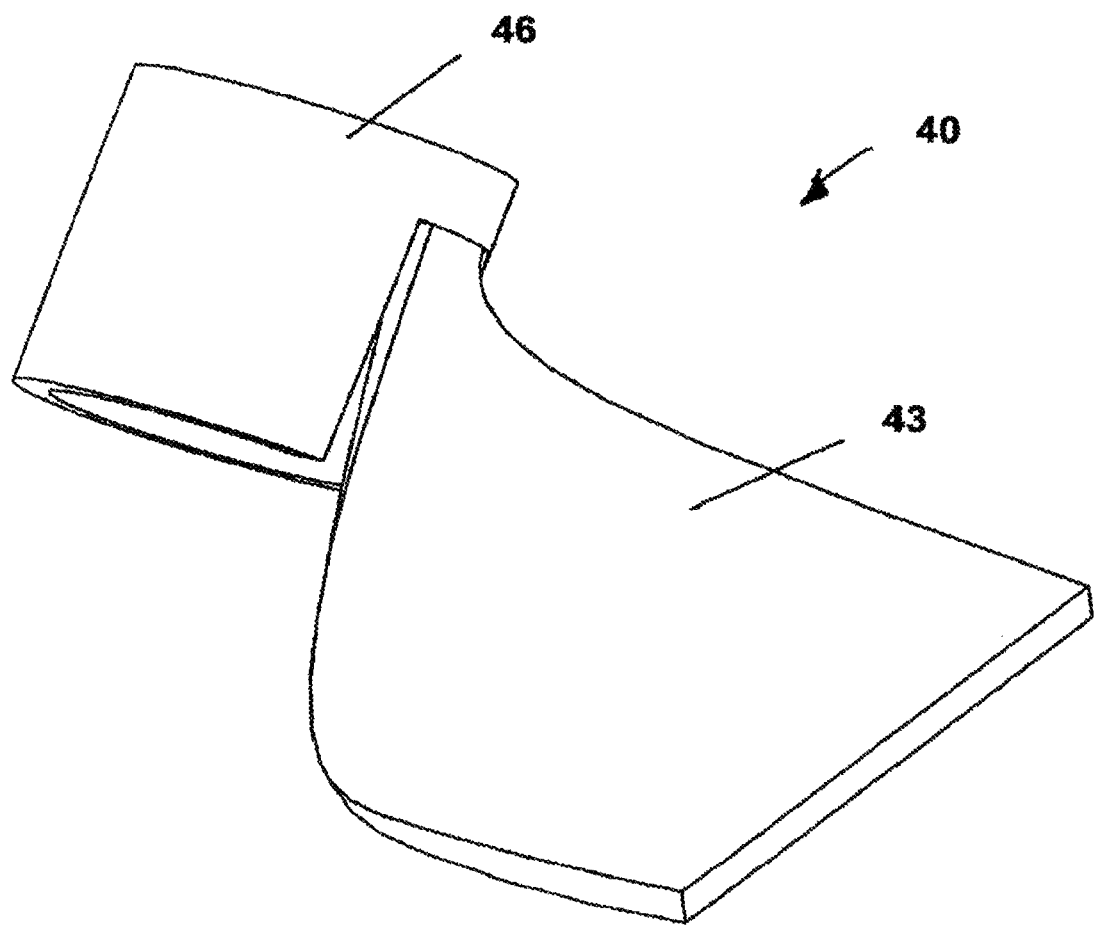

FIG. 13a shows a rotor segment 40 which consists of a hub segment 46 and also a lamella 43 connected thereto in one part. The rotor segment is produced from a pipe material, the hub segment 46 essentially still having the diameter of the pipe (of concern hereby is also a ring closed in regions) and the lamella being bent therefrom. For this purpose, the lamella is cut out firstly in its original form by means of a laser beam and subsequently plastic deformability on a molded body is achieved in which the deformation state shown in FIG. 13a is produced. Subsequently, the result is also an etching treatment and for other surface treatment of the lamellae. In order to produce a final blade (see FIG. 13c), a plurality of rotor segments are then disposed axially relative to each other.

Also, an individual lamella can hereby be covered with a plastic material or metal foil/membrane or also can be sprayed-around and/or molded in order to achieve a greater surface.

Figure 13B:
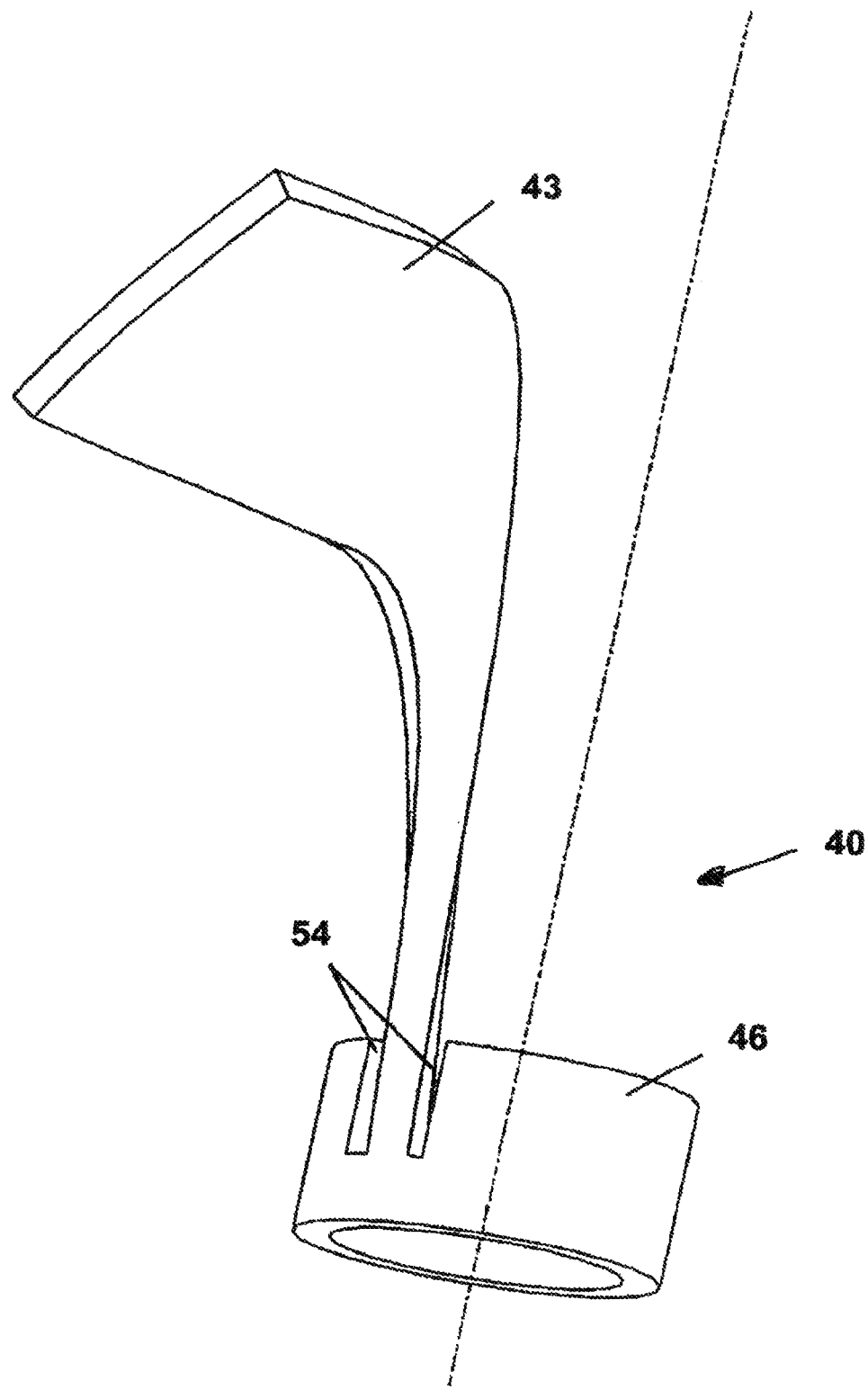

FIG. 13b shows another 'view of the rotor segment 40, it can be seen here how tension relieving slots 54 are shown in the foot region of the lamella 43.

It can be seen that the rotor segment shown in FIG. 13a/13b has a closed annular shape in the lower region of the hub segment. In addition, it can be seen that the rotor segment connects the hub segment and also the lamella in one part.

FIG. 13d shows a further embodiment of a rotor segment which is cut from a pipe material and is not yet completely finished, in the case of which rotor segment the lamellae 43, 43a are not yet spread out. Here also, tension-relieving slots 54 can however already be seen, in particular also form-fitting elements 47 in the form of raised portions can be seen, which can engage in corresponding depressions of axially adjacent rotor segments in order hence to fix the position of the lamellae (later radially spread out).

A rotor with a blade 42 according to the invention is shown in detail again in FIG. 13d. The preferred conveying direction of the rotor is hereby characterized by the right-side rotational arrow, it consequently results that the flow pressure side 51 and the (opposite side of the lamellae) is the flow suction side 52. Here a plurality of rotor segments 40 is disposed axially adjacently by their respective hub segments 46. There is consequently produced also a stepping of the adjacent lamellae 43, 44, 45 which are disposed on a rotor shaft 41. This rotor shown in FIG. 13d can be part of a fluid pump shown in FIG. 8, in particular an intraventricular catheter pump. This is a catheter pump for introduction into human vessels, the rotor with a blade being disposed in the distal end region of the catheter pump and the pump having a conveying direction for conveying body fluid from distal to proximal and the blade having a flow pressure side 51 (see above) and a flow suction side 52.

It can be readily seen in FIG. 13d that, on the flow pressure side 51, the proximal region of the distal lamella 44 covers the distal region of the proximal lamella 43. The result consequently is formation of a closed blade, at least in the radial outer region of the lamellae. The lamellae are hereby configured "in the shape of an ice hockey stick". Consequently, a very good overlap in the relevant flow region is produced, in addition good collapsibility. Finally, even with a high fluid counterpressure, only a small flow loss results due to the above-mentioned orientation of the stepping of the lamellae.

In addition, it is shown in FIG. 13d that application of the lamellae 43, 44, 45 in a compressed state is effected essentially by deflecting the lamellae in the direction of the flow pressure (see arrow 53). This arrow is shown once in the distal and once in the proximal region of the rotor. The "ice hockey stick-shaped" design of the lamellae offers the advantage in addition that, when inserting into a lock situated proximally of the rotor, a low-force and entanglement-free insertion of the rotor is produced.

Figure 13E:
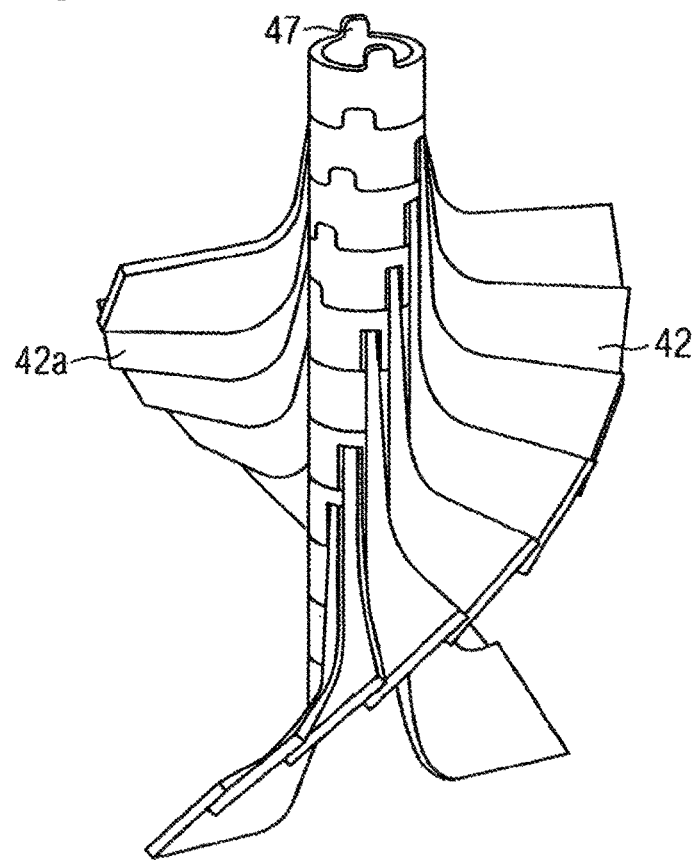

FIG. 13e shows a further embodiment of a rotor according to the invention in which two blades 42 and 42a are provided. The rotor shown in FIG. 13e is a combination of a plurality of rotor segments according to FIG. 13c.

Figure 13F:
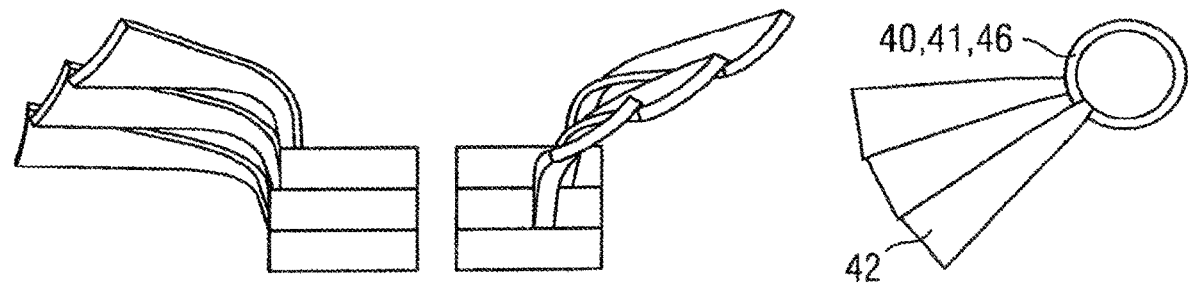

FIG. 13f shows a combination of three rotor segments 40 which form parts of a rotor shaft 41, also three hub segments are hereby disposed in succession, a common blade 42 is produced.

Figure 13G:
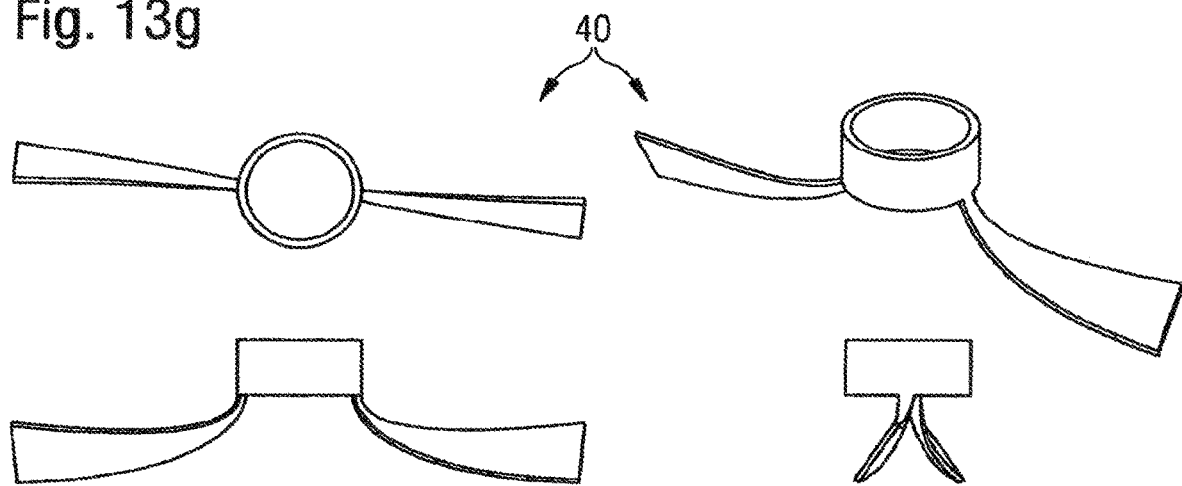
Figure 13H:
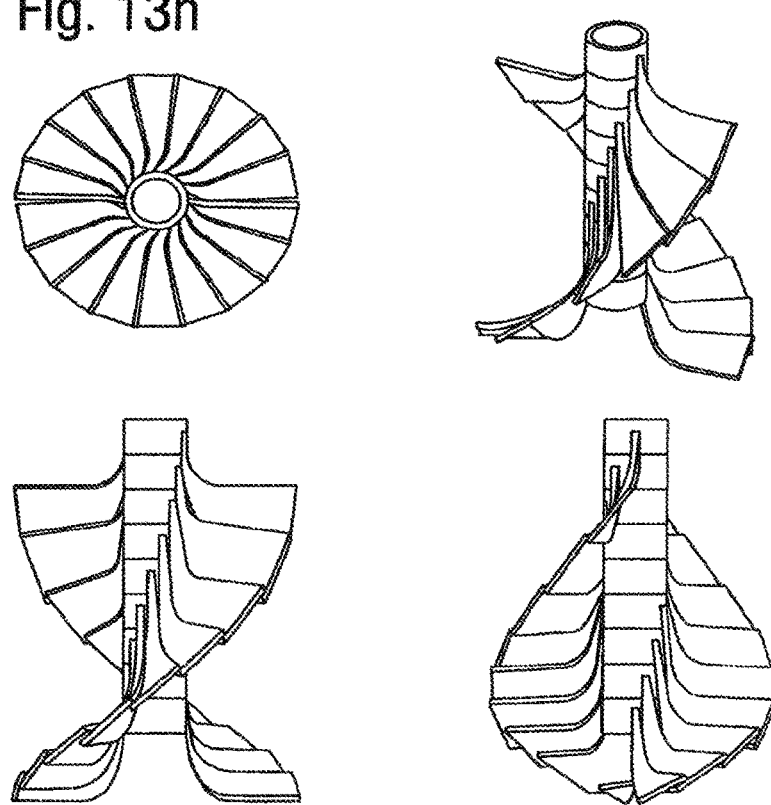
Figure 13I:
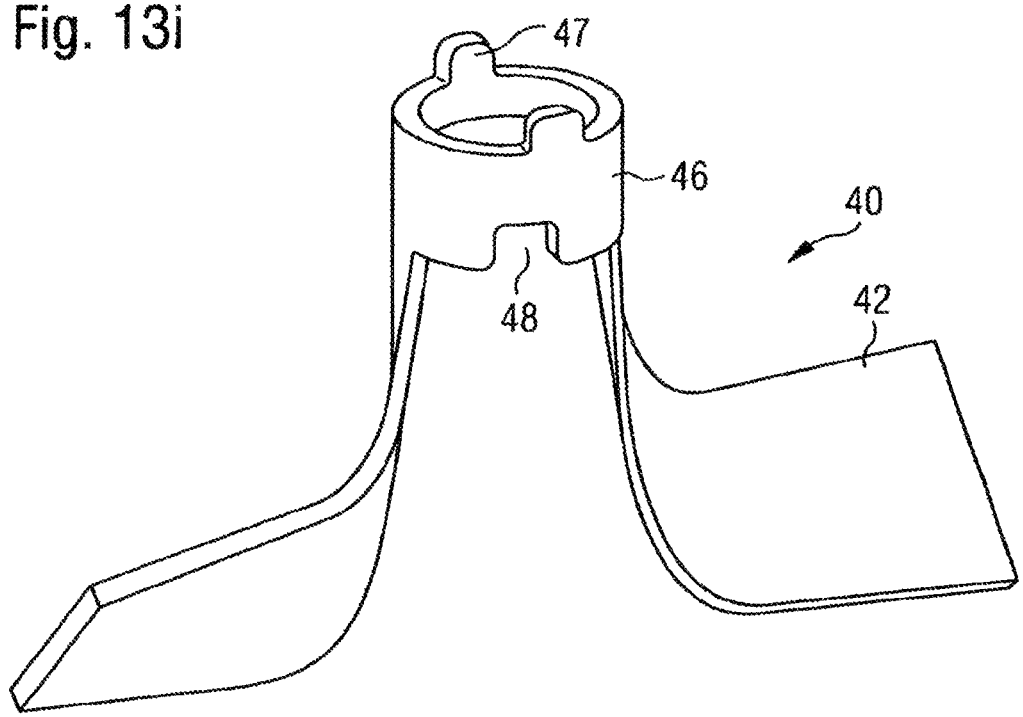
Figure 13J:
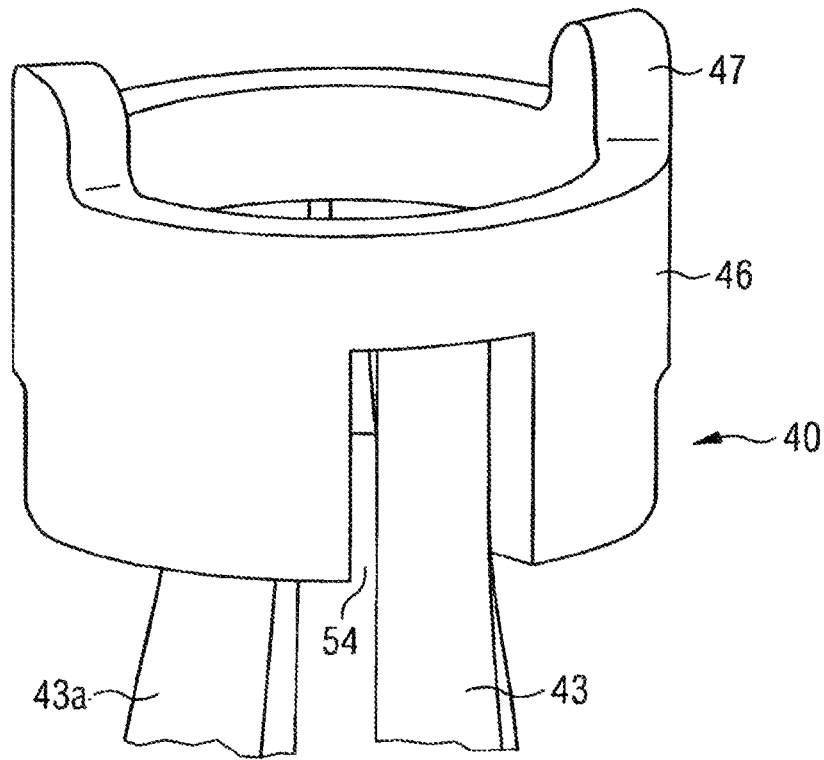

FIG. 13g shows a simple embodiment of a rotor segment 40 with two lamellae protruding radially therefrom. FIG. 13h shows further embodiments of rotors according to the invention. FIGS. 13i and 13j again show the rotor segment shown in FIG. 13c, here once again the tension-relieving slots 54 and also the form-fitting end serving for the form-fit being shown even better with 47 (raised portion) and also 48 (concavity).

Figure 13K:
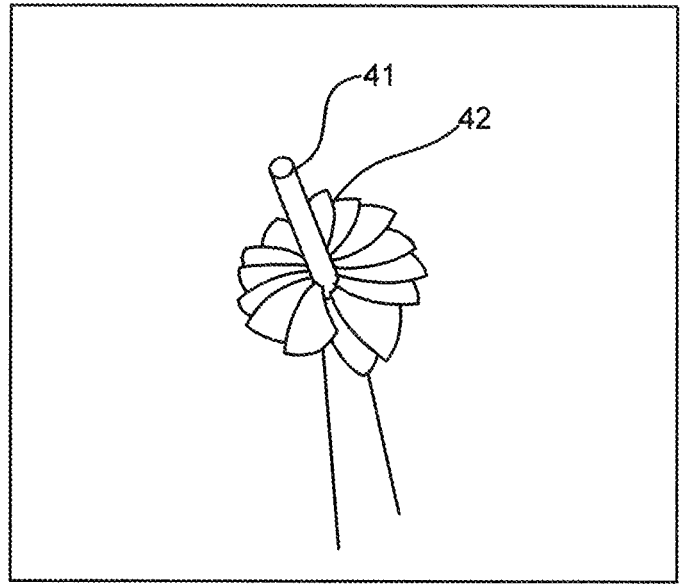
Figure 13L:
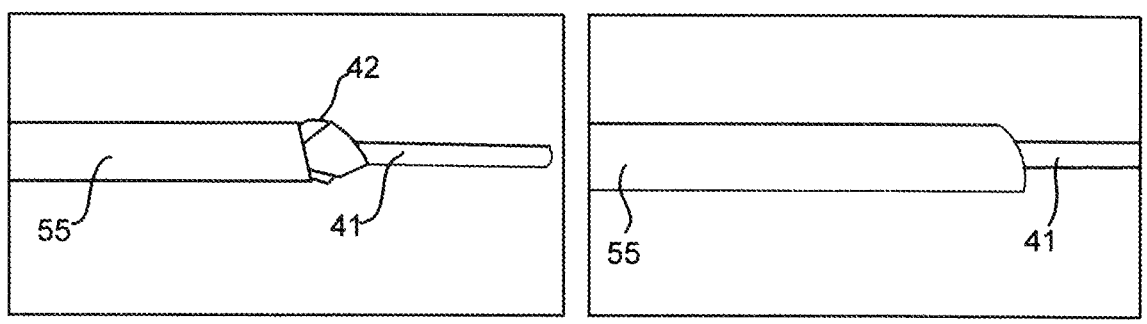

FIG. 13k shows a blade 42 on a rotor shaft 41, FIG. 13l shows two photographs in which, in the left picture, a blade 42 made of a plurality of lamellae is drawn into an insertion lock 55, the rotor shaft 41 can be seen on the right side. In the right-side picture, the blade 42 is completely inserted in the insertion lock 55.

Figure 14A:
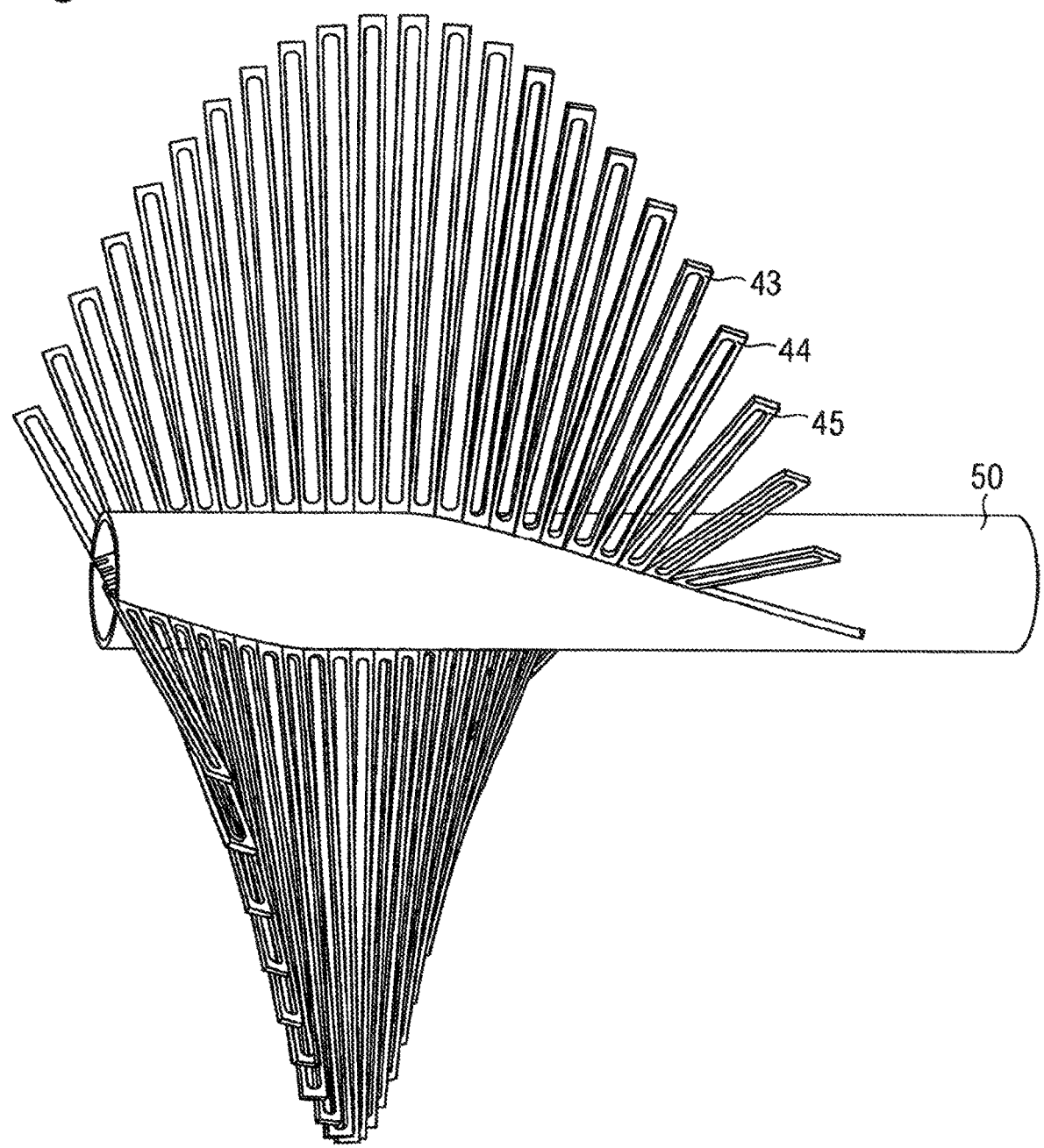
Figure 14B:
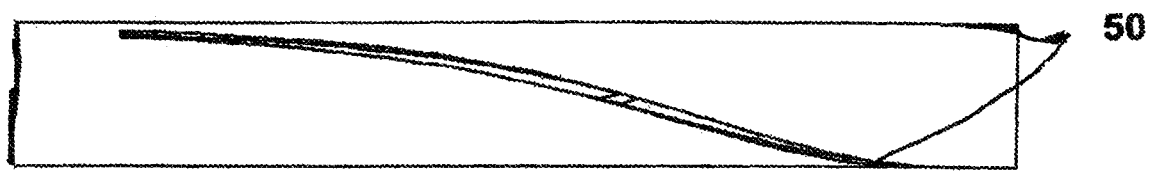
Figure 14C:
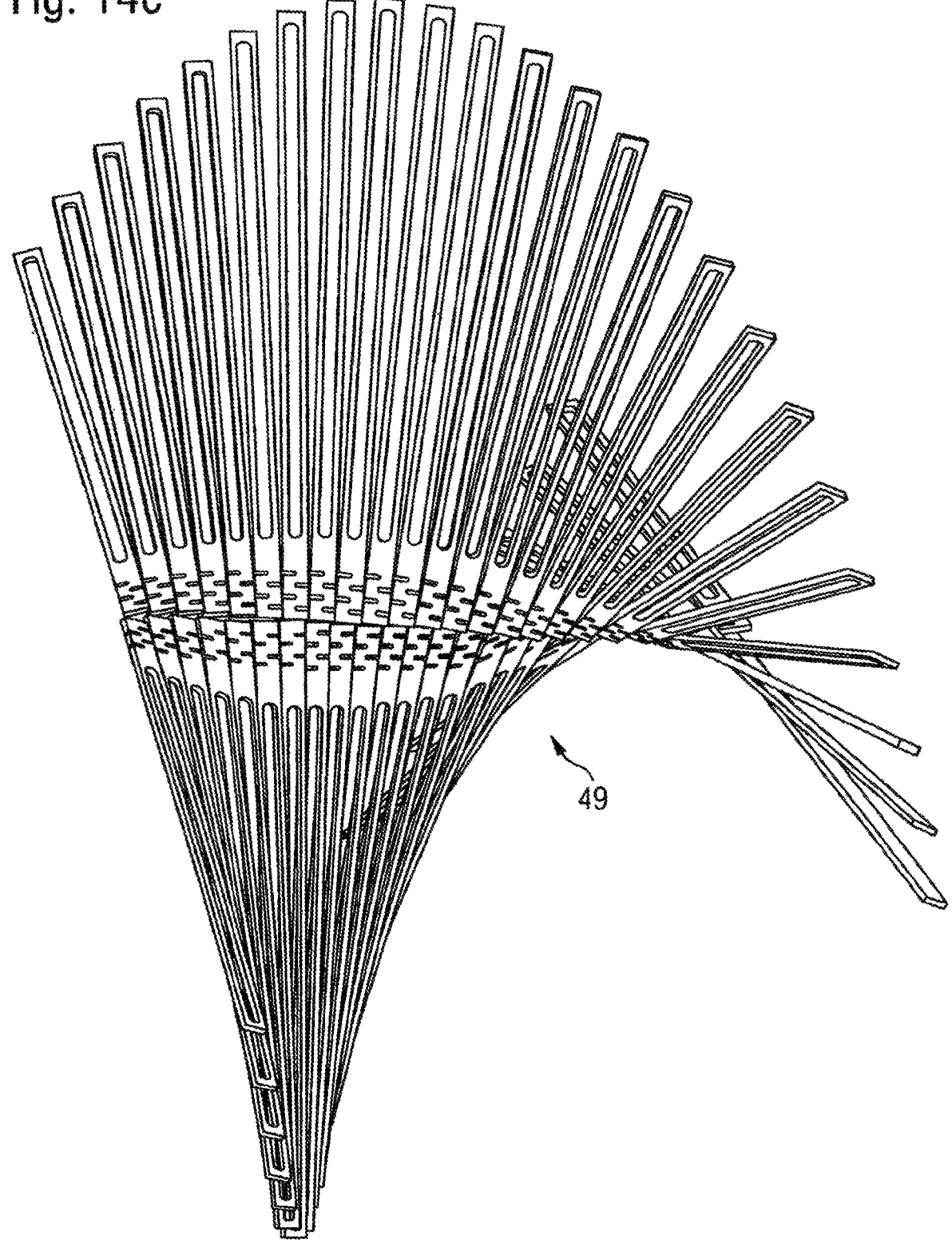
Figure 14D:
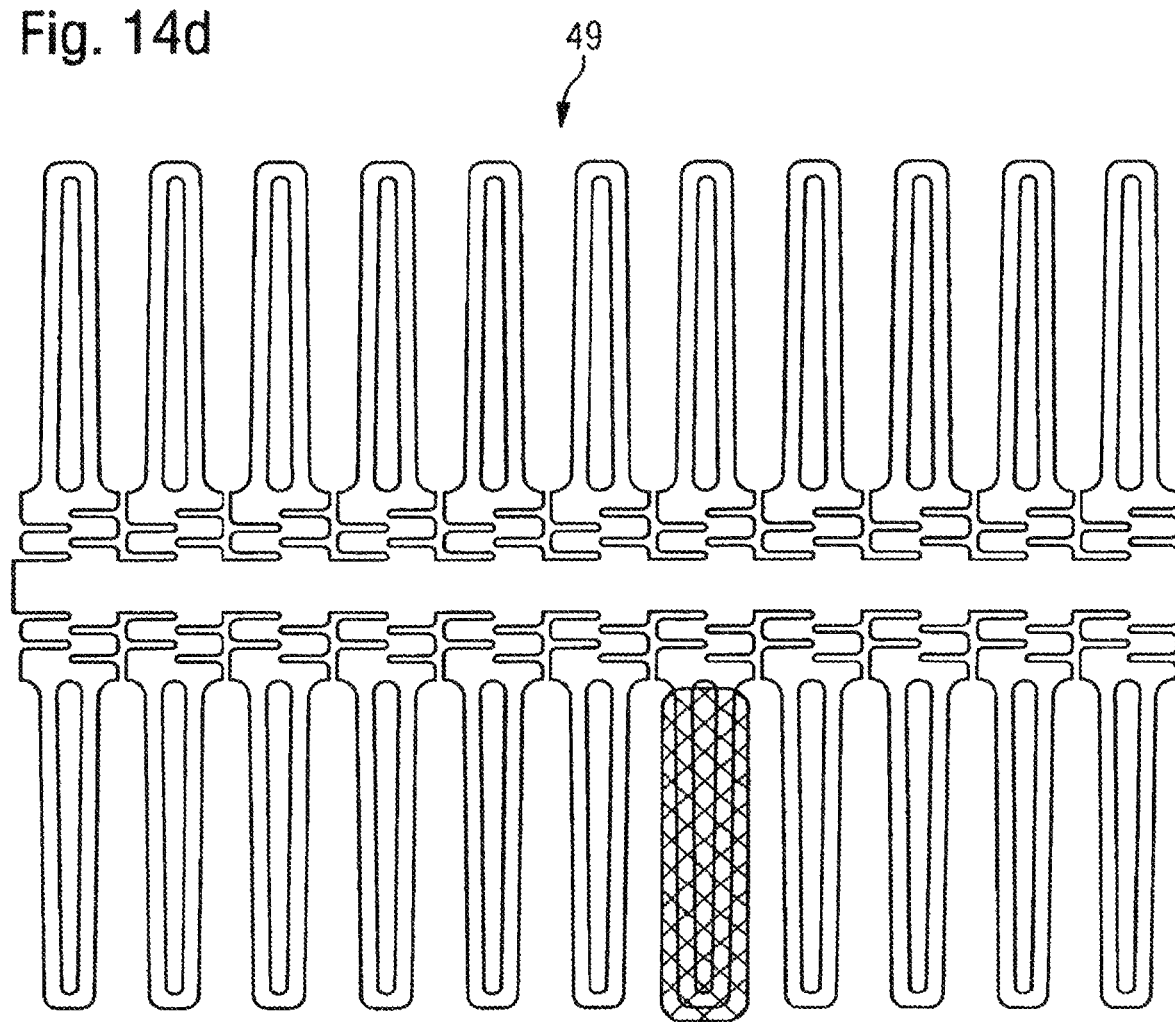

FIG. 14a shows a further embodiment of a rotor in which a hub body 50 has two spiral slots (see FIG. 14b) into which a lamella body 49 (see FIG. 14c) is inserted. The view of a flat material from which the lamella body 49 is cut by means of a laser can be seen in FIG. 14d. For clarification, a possible spraying-around/covering of a lamella is also shown once again in FIGS. 14d and/or 15a (with cross hatching). The cross hatching can, in another embodiment, be understood that the entire cross-hatched area is made of flat material.

Figure 15A:
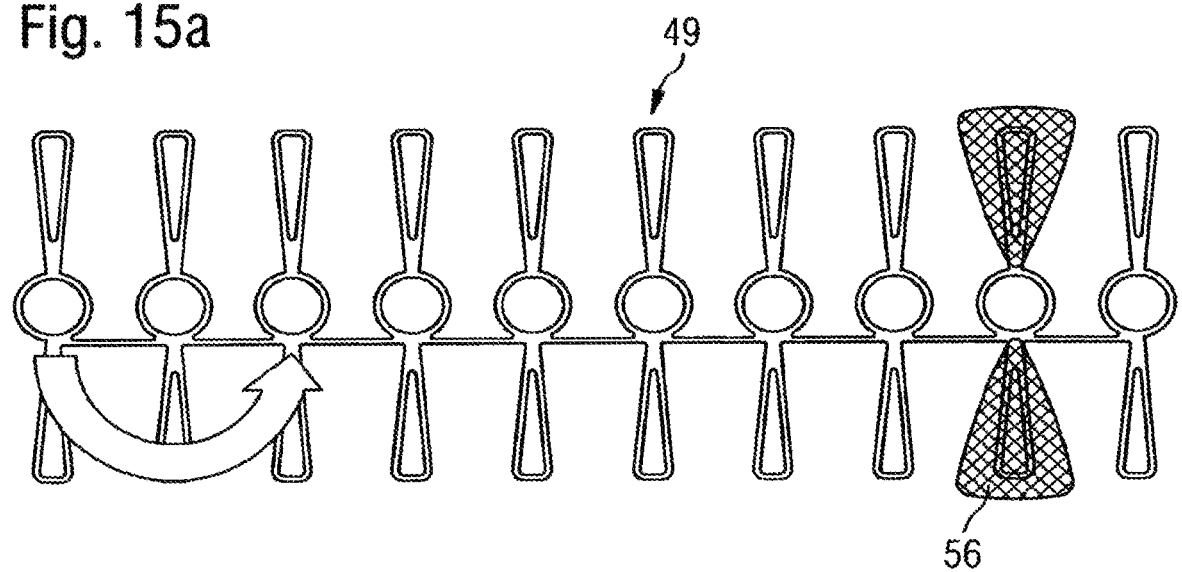
Figure 15B:
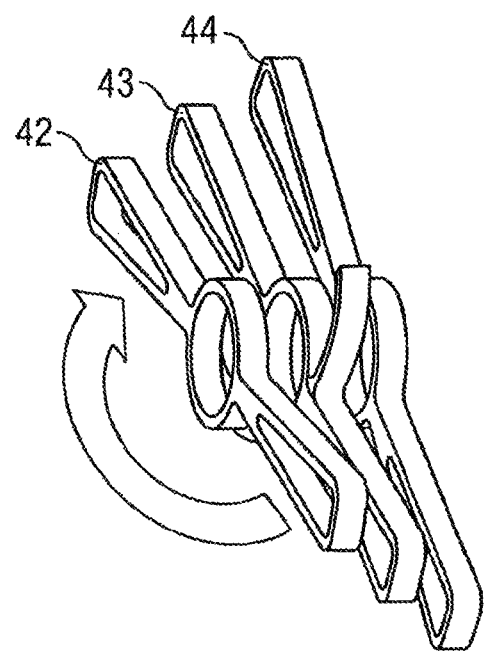

In FIGS. 15a and 15b, a further embodiment of a blade is shown. A lamella basic body 49 is hereby cut from a flat material, connection struts being provided between individual rotor segments. In that the individual rotor segments are tilted out of the surface plane and recombined with each other; a helical structure is then produced automatically. This functions for example in such a manner that, according to FIG. 15a, the rotor segment disposed on the left side is rotated out of the plane and placed on the next element from the left (and so on for the other rotor elements) such that the openings of the hub segment overlap each other. If these hub segments are then disposed on a common rotor shaft, a helical arrangement of the lamellae 42, 43, 44 is produced automatically. The lamellae may, in a subsequent forming process, be rotated in respect of their longitudinal axis in order to achieve overlapping of the lamellae.

The invention claimed is:

1. A compressible and expandable rotor for a fluid pump, the rotor comprising:
    a plurality of individual rotor segments, each individual rotor segment including a hub segment and at least one lamella extending from the hub segment,
    wherein each hub segment is attachable to at least one axially adjacent hub segment such that the hub segments of the plurality of individual rotor segments form a rotor shaft and, when the rotor is in an expanded state, the lamellae of the plurality of individual rotor segments form a continuous rotor blade.

2. The rotor of claim 1, wherein the rotor is rotatable about an axis of rotation extending along the rotor shaft.

3. The rotor of claim 2, wherein, when the rotor is rotated in a first direction about the axis of rotation, the rotor is expanded to the expanded state under fluid counter-pressure.

4. The rotor of claim 3, wherein the continuous rotor blade is configured to convey fluid in a conveying direction when the rotor is rotated in the first direction.

5. The rotor of claim 4, wherein the conveying direction extends from a distal end of the rotor to a proximal end of the rotor.

6. The rotor of claim 1, wherein each lamella is pivotable relative to an axis of rotation of the rotor to enable the rotor to compress and expand.

7. The rotor of claim 1, wherein, when the rotor is in the expanded state, adjacent lamellae are configured to abut against each other to form the continuous blade.

8. The rotor of claim 7, wherein, when the rotor is in the expanded state, adjacent lamellae are configured to overlap with each other in at least a portion of each adjacent lamella.

9. The rotor of claim 1, wherein the continuous rotor blade extends helically about the rotor shaft.

10. The rotor of claim 1, wherein each hub segment includes at least one engaging element that is configured to engage at least one receiving element of an axially adjacent hub segment.

11. The rotor of claim 10, wherein the at least one engaging element is a raised portion of the hub segment.

12. The rotor of claim 10, wherein the at least one receiving element is a depression in the hub segment.

13. The rotor of claim 1, wherein each hub segment has an annular shape.

14. The rotor of claim 1, wherein adjacently attached hub segments are not rotatable relative to each other.

15. The rotor of claim 1, wherein the at least one lamella of each individual rotor segment comprises a first lamella and a second lamella that each extend from the hub segment.

16. The rotor of claim 15, wherein the first lamella and second lamella attach to and extend from opposite sides of the hub segment.

17. The rotor of claim 16, wherein, when the rotor is in the expanded state, the first lamellas of the plurality of individual rotor segments form a first continuous rotor blade and the second lamellas of the plurality of individual rotor segments form a second continuous rotor blade.

18. The rotor of claim 17, wherein the first and second continuous rotor blades extend helically about the rotor shaft.

19. A pump assembly comprising:
    a catheter;
    a compressible and expandable rotor disposed at a distal portion of the catheter, the rotor comprising a plurality of individual rotor segments, each individual rotor segment including a hub segment and at least one lamella extending from the hub segment, wherein each hub segment is attachable to at least one axially adjacent hub segment such that the hub segments of the plurality of individual rotor segments form a rotor shaft and, when the rotor is in an expanded state, the lamellae of the plurality of individual rotor segments form a continuous rotor blade; and
    a compressible and expandable pump housing surrounding the rotor.

20. The pump assembly of claim 19, further comprising a motor configured to rotate the rotor about an axis of rotation.

21. The pump assembly of claim 19, wherein, when the rotor is rotated in a first direction about an axis of rotation, the rotor is expanded to the expanded state under fluid counter-pressure.

22. The pump assembly of claim 19, further comprising a sheath, the catheter extending through the sheath.

23. The pump assembly of claim 22, wherein the sheath is configured to compress the pump housing and the rotor to a compressed state when the pump housing is pulled into the sheath.

* * * * *